United States Patent [19]

Donahue et al.

[11] Patent Number: 5,484,768
[45] Date of Patent: Jan. 16, 1996

[54] TREATMENT OF MALE INFERTILITY BY ADMINISTRATION OF A MUELLERIAN INHIBITING SUBSTANCE AND SURGERY AND/OR HORMONAL TREATMENT

[75] Inventors: Patricia K. Donahue, Weston, Mass.; John M. Hutson, East Malvern, Australia

[73] Assignee: The University of Melbourne, Parkville, Australia

[21] Appl. No.: 960,387
[22] PCT Filed: Jul. 9, 1991
[86] PCT No.: PCT/US91/04806
  § 371 Date: Mar. 8, 1993
  § 102(e) Date: Mar. 8, 1993
[87] PCT Pub. No.: WO92/00752
  PCT Pub. Date: Jan. 23, 1992

[30] Foreign Application Priority Data

Jul. 10, 1990 [AU] Australia ................. 1093/90

[51] Int. Cl.⁶ .................................. A61K 38/22
[52] U.S. Cl. .................. 514/2; 514/21; 424/559
[58] Field of Search ............ 514/2, 21; 424/559

[56] References Cited

U.S. PATENT DOCUMENTS 4,404,188  9/1983  Donahoe et al. ............... 424/105
4,510,131  4/1985  Donahoe et al. ............... 424/105

OTHER PUBLICATIONS

Meyers-Waller et al., Biol Reprod 41(5):881-888 1989 Abstract BA 89(7):77198.
Luthra et al., Pediatric Surg Int 4(4):260-264 (1989) Abstract BA 88(8):82764.
Scott, B. R. J Urol 60(1):74-76 (1987) Abstract BA 84(9):92880.
Bercu et al., Pediatr Res 13(4 Part 1):246-249 (1979) Abstract BA 68(6):37053.
Ueno et al., Endocrinology 123(3):1652-1659 (1988) Abstract BA 86(10): 101496.

Primary Examiner—Marian C. Knode
Assistant Examiner—Jean C. Witz
Attorney, Agent, or Firm—Sterne, Kessler, Goldstein & Fox

[57] ABSTRACT

A method for the treatment of infertility associated with undescended testes in male animals is disclosed. Also disclosed is a method for effecting testicular germ cell maturation.

These methods involve administering to a subject in need of such treatment a therapeutically effective amount of Mullerian inhibiting substance (MIS) or an analogue thereof having MIS activity.

MIS may be administered to a subject shortly after treatment to effect testes descent and/or prior to testes descent.

29 Claims, 5 Drawing Sheets

```
-200  cacatcaggcccagctctatcactggggagggagataggctgccagggac
      agaaagggctctttgagaaggccactctgcctggagtgggggcgccgggc  -101
-100  actgtcccccaaggtcgaggcagaggagataggggtctgtcctgcacaaa
      cacccccaccttccactcggctcacttaaggcaggcagcccagcccctggc  -1
   1  agcacccacgATGCGGGACCTGCCTCTCACCAGCCTGGCCCTAGTGCTGT
             M  R  D  L  P  L  T  S  L  A  L  V  L  S
      CTGCCCTGGGGGCTCTGCTGGGGACTGAGGCCCTCAGAGCAGAGGAGCCA     100
       A  L  G  A  L  L  G  T  E  A  L  R  A  E  E  P
 101  GCTGTGGGCACCAGTGGCCTCATCTTCCGAGAAGACTTGGACTGGCCTCC
       A  V  G  T  S  G  L  I  F  R  E  D  L  D  W  P  P
      AGGCATCCCACAAGAGCCTCTGTGCCTGGTGGCACTGGGCGGGGACAGCA     200
       G  I  P  Q  E  P  L  C  L  V  A  L  G  G  D  S  N
 201  ATGGCAGCAGCTCCCCCCTGCGGGTGGTGGGGGCTCTAAGCGCCTATGAG
         G  S  S  S  P  L  R  V  V  G  A  L  S  A  Y  E
      CAGGCCTTCCTGGGGGCCGTGCAGAGGGCCCGCTGGGGCCCCCGAGACCT     300
       Q  A  F  L  G  A  V  Q  R  A  R  W  G  P  R  D  L
 301  GGCCACCTTCGGGGTCTGCAACACCGGTGACAGGCAGGCTGCCTTGCCCT
       A  T  F  G  V  C  N  T  G  D  R  Q  A  A  L  P  S
      CTCTACGGCGGCTGGGGGCCTGGCTGCGGGACCCTGGGGGGCAGCGCCTG     400
       L  R  R  L  G  A  W  L  R  D  P  G  G  Q  R  L
 401  GTGGTCCTACACCTGGAGGAAGgtatgtggggcccagccccaagcttggc
       V  V  L  H  L  E  E
      accgccgtcttccttcaggtgggccgggtcctcctagggaagatcagggg     500
 501  ctggcagagcccccaccctgggcagggaggctgtggtcttgttcctagga
      ctgggttgcgggtccgtggcctggaagggtgggcaccacactctgtcctgt     600
 601  ccccgaagcccagctcttagacttgccctgcctcggtgccagggagaga
      gctgctgccttctccccaccctgaagacgacgcagggctcgggggccagt     700
 701  ggaaccttcttcccacagccccagcctgttctcagggccgctggcctaa
      gatactccctgcggggaaggggcttcatcgggcaccccaacccagagacc     800
 801  ccagggcggcagccccacccacagcctcagacgcagcccctgcctgcccc
      tgccgtcaccgctccctggctgcaggaaggcagctaagaggggcacccctt     900
 901  gtcccccgcttgaggtccctgcacagtggccagagcggcagggacagat
      cccaaagattcccggggggtgtggccttcaatggctcaggcgtcccctgc    1000
1001  tgtcccggctgcagTGACCTGGGAGCCAACACCCTCGCTGAGGTTCCAGG
                     V  T  W  E  P  T  P  S  L  R  F  Q  E
      AGCCCCCGCCTGGAGGAGCTGGCCCCCCAGAGCTGGCGCTGCTGGTGCTG    1100
       P  P  P  G  G  A  G  P  P  E  L  A  L  L  V  L
```

FIG.3A

```
1101 TACCCTGGGCCTGGCCCTGAGGTCACTGTGACGAGGGCTGGGCTGCCGGG
      V  P  G  P  G  P  E  V  T  V  T  R  A  G  L  P  G
     TGCCCAGgtaccagggagttgcatggggcagtgcccgggccgtggcgggg    1200
      A  Q
1201 ggcatgaatttgttgcagggtctgcagtactgagaacagcgtagaaccag
     tggcgatggggaggaaggggaccggtagagcggggctgggtaagcctccat   1300
1301 ccagccgggctgagccctggtctccgcagAGCCTCTGCCCCTCCCGAGAC
                                   S  L  C  P  S  R  D
     ACCCGCTACCTGGTGTTAGCGGTGGACCGCCCTGCGGGGGCCTGGCGCGG   1400
      T  R  V  L  V  L  A  V  D  R  P  A  G  A  W  R  G
1401 CTCCGGGCTGGCCTTGACCCTGCAGCCCCGCGGAGAGGgtaggtccgcgt
      S  G  L  A  L  T  L  Q  P  R  G  E
     ggagagggacggggagccgggtcgactgcccccgggcccccagcccctga   1500
1501 gccagccgcgtgcccacccaccgcagACTCCCGGCTGAGTACCGCCCGGC
                                D  S  R  L  S  T  A  R  L
     TGCAGGCACTGCTGTTCGGCGACGACCACCGCTGCTTCACACGGATGACC   1600
      Q  A  L  L  F  G  D  D  H  R  C  F  T  R  M  T
1601 CCGGCCCTGCTCCTGCTGCCGCGGGTCCGAGCCCGCGCCGCTGCCTGCGCA
      P  A  L  L  L  L  P  R  S  E  P  A  P  L  P  A  H
     CGGCCAGCTGGACACCGTGCCCTTCCCGCCGCCCAGgtgcgcgcaggcac   1700
      G  Q  L  D  T  V  P  F  P  P  P  R
1701 cgggacacggggcaggagcgggcgggggcggcgtggcctcgtggccgctc
     tcaactcctccaattgcgggttccagGCCATCCGCGGAACTCGAGGAGTC   1800
                                P  S  A  E  L  E  E  S
1801 GCCACCCAGCGCAGACCCCTTCCTGGAGACGCTCACGCGCCTGGTGCGGG
      P  P  S  A  D  P  F  L  E  T  L  T  R  L  V  R
     CGCTGCGGGTCCCCCCGGCCCGGGCCTCCGCGCCGCGCCTGGCCCTGGAT   1900
      L  R  V  P  P  A  R  A  S  A  P  R  L  A  L  D
1901 CCGGACGCGCTGGCCGGCTTCCCGCAGGGCCTAGTCAACCTGTCGGACCC
      P  D  A  L  A  G  F  P  Q  G  L  V  N  L  S  D  P
     CGCGGCGCTGGAGCGCCTACTCGACGGCGAGGAGCCGCTGCTGCTGCTGC   2000
      A  A  L  E  R  L  L  D  G  E  E  P  L  L  L  L
2001 TGAGGCCCACTGCGGCCACCACCGGGGATCCTGCGCCCCTGCACGACCCC
         R  P  T  A  A  T  T  G  D  P  A  P  L  H  D  P
     ACGTCGGCGCCGTGGGCCACGGCCCTGGCGCGCCGCGTGGCTGCTGAACT   2100
      T  S  A  P  W  A  T  A  L  A  R  R  V  A  A  E  L
2101 GCAAGCGCCGGCTGCCGAGCTGCGAAGCCTCCCGGGTCTGCCTCCGGCCA
      Q  A  A  A  A  E  L  R  S  L  P  G  L  P  P  A  T
```

FIG. 3B

```
            CAGCCCCGCTGCTGGCGCGCCTGCTCGCGCTCTGCCCAGGAGGCCCCGGC  2200
              A  P  L  L  A  R  L  L  A  L  C  P  G  G  P  G
    2201  GGCCTCGGCGATCCCCTGCGAGCGCTGCTGCTCCTGAAGGCGCTGCAGGG
            G  L  G  D  P  L  R  A  L  L  L  L  R  A  L  Q  G
          CCTGCGCGTGGAGTGGCGCGGGCGGGATCCGCGCGGGCCGGGTCGGGCAC  2300
            L  R  V  E  W  R  G  R  D  P  R  G  P  G  R  A  Q
    2301  AGCGCAGCGCGGGGGCCACCGCCGCCGACGGGCCGTGCGCGCTGCGCGAG
            R  S  A  G  A  T  A  A  D  G  P  C  A  L  R  E
          CTCAGCGTAGACCTCCGCGCCGAGCGCTCCGTACTCATCCCCGAGACCTA  2400
            L  S  V  D  L  R  A  E  R  S  V  L  I  P  E  T  V
    2401  CCAGGCCAACAATTGCCAGGGCGTGTGCGGCTGGCCTCAGTCCGACCGCA
            Q  A  N  N  C  Q  G  V  C  G  W  P  Q  S  D  R  N
          ACCCGCGCTACGGCAACCACGTGGTGCTGCTGCTGAAGATGCAGGCCCGT  2500
            P  R  V  G  N  H  V  V  L  L  L  R  M  Q  A  R
    2501  GGGGCCGCCCTGGCGCGCCCACCCTGCTGCGTGCCCACCGCCTACGCGGG
            G  A  A  L  A  R  P  P  C  C  V  P  T  A  V  A  G
          CAAGCTGCTCATCAGCCTGTCGGAGGAACGCATCAGCGCGCACCACGTGC  2600
            R  L  L  I  S  L  S  E  E  R  I  S  A  H  H  V  P
    2601  CCAACATGGTGGCCACCGAGTGTGGCTGCCGGtgaccCctgcgccgcgcg
            N  M  V  A  T  E  C  G  C  R
          gactcctgccccgagggtccggacgcgccccagctcgcgccccttcccat  2700
    2701  atttattcggaccccaagcatcgccccaataaagaccagcaagcaaccgg
          ctggggtgtccgtgcgtgttagggggcccgtgggacctcccttgccgtct  2800
    2801  ctcctcgcgcacggcccgggtccgccctgtagcgctcgctgtctctcccc
          tgcctgaagcgccccaccaccgtctttcaggccccggacttggtgccggg  2900
```

FIG.3C

TREATMENT OF MALE INFERTILITY BY ADMINISTRATION OF A MUELLERIAN INHIBITING SUBSTANCE AND SURGERY AND/OR HORMONAL TREATMENT

FIELD OF THE INVENTION

This invention relates to a method for the treatment of male infertility associated with undescended testes.

The testes are two glandular organs which secrete semen, and are situated in the scrotum, being suspended by the spermatic cords.

DESCRIPTION OF THE BACKGROUND ART

For the last 40–50 years it has been known that testicular descent is controlled by male androgenic hormones (testosterone). Androgens were proposed to act directly or indirectly on mesenchymal tissue in the groin known as the gubernaculum, which migrates across the pubic region from the groin to the scrotum during inguino-scrotal testicular descent. The gubernaculum was thought to guide the testes into the scrotum.

In humans, approximately 5% of male babies are born with undescended testes. In 1–2% of males the testes remain undescended while the remainder descend in the first few months. Normally, the testes are fully descended by 30–36 weeks gestation. Testes descending postnatally are not quite normal and many re-ascend out of the scrotum later in childhood.

The treatment for undescended testes is either invasive surgery (orchidopexy), where the undescended organ is physically transferred to the scrotum, or hormonal therapy, which in a small number of children may stimulate descent without operation.

One of the main complications of undescended testes, and a primary reason for surgical intervention, is the risk of subsequent infertility. Many boys, however, have undergone successful repositioning of the testis in the scrotum but have suffered persisting infertility which has not been corrected by surgery.

Chivers et al. (J. Ped. Surg. 21, 691, 1986) have described the frequency of azospermia (no sperm production) or oligospermia (insufficient sperm production) in males suffering from one (unilateral) or two (bilateral) undescended testicles, either without treatment, after surgical repositioning of the testes (orchidopexy), or offer both orchidopexy and hormone treatment with HCG (human chorionic gonadotrophin). The results obtained by Chivers et al. are as follows:

|  | Frequency of Azospermia | |
|---|---|---|
|  | Bilateral | Unilaterial |
| No treatment | 100% | 44% |
| Orchidopexy | 74% | 41% |
| HCG and orchidopexy | 73% | 49% |

It is clear from the results that sperm production is quite low even after orchidopexy, and that hormone treatment has little effect.

The function of the testis is very dependent on its temperature, with the best function at 33° C., this being 4° C. below normal internal body temperature. The reason that the testis normally resides in the scrotum is to provide a low-temperature environment which provides the maximum viability of spermatozoa stored in the adjacent epididymis.

Where the testis remains out of the scrotum during childhood, progressive changes of degeneration are observed. The germ cells of the testis progressively disappear between 6 months and 2 years, while the interstitial tissue between the seminiferous tubules becomes thicker. The tubules themselves eventually become small and atrophic.

The germ cells are present in large numbers in the tubules at birth, and they have the appearance of primitive germ cells. Between about 4 months and 2 years these germ cells undergo a crucial series of developmental steps or "transformations", so that they end up with the appearance of "primary spermatocytes". The sequence of cell types involved in the transformation is:

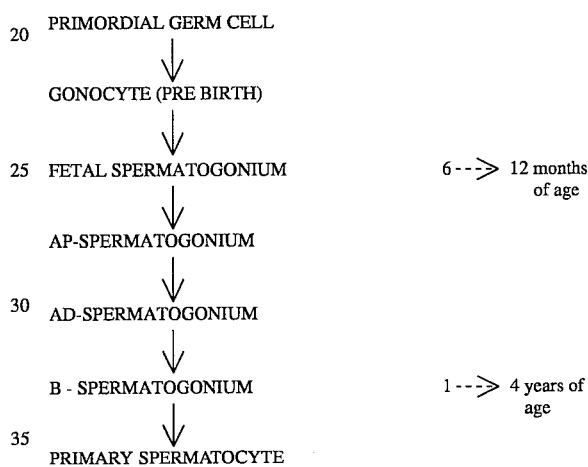

During this transformation phase the total number of germ cells falls even in normal testes, but then the primary spermatocytes "repopulate" the tubules. The transformation phase does not occur normally in undescended testes and this is believed to account for the subsequent infertility (Huff et al., 1989, J. Immonol. 142: 506–508).

Some advocates of hormonal therapy, which has now been shown to be successful in only a small percentage of boys (Rajfer et al, 1986, N. Eng. J. Med., 314: 466–470; De Munick Keizer-Schrama et al, 1986, Lancet 11: 876–879), have suggested that gonadotrophin hormones might still have a role in stimulating germ cell development after surgical intervention. The mechanism by which gonadotrophins may act is not known.

DETAILED DESCRIPTION OF THE INVENTION

Applicants have discovered that MIS is involved in germ cell maturation, and that MIS may be used to effect germ cell maturation, as well as for the treatment of infertility associated with undescended testes.

In accordance with an aspect of this invention, there is provided a method for the treatment of infertility associated with undescended testes in male animals which comprises administering to a subject in need of treatment a therapeutically effective amount of Mullerian inhibiting substance (hereafter MIS) or an analogue thereof optionally in association with a carrier and/or excipient.

In accordance with a second aspect of this invention, there is provided a method for effecting testicular germ cell maturation which comprises administering to a subject in need of such treatment MIS or an analogue thereof optionally in association with a carrier and/or excipient.

In another aspect, the invention relates to a pharmaceutical composition for the treatment of infertility associated with undescended testes in male animals, which comprises MIS or an analogue thereof in association with a pharmaceutically acceptable carrier and/or excipient.

In a further aspect, this invention relates to the use of MIS or an analogue thereof in the manufacture of a medicament for the treatment of infertility associated with undescended testes.

MIS is a large glycoprotein (MW 140,000 Daltons) comprised of 2 peptide chains linked by disulphide bonds. It is produced by the Sertoli cells in the seminiferous tubules of the testes and derives its name from its first known function, that of causing regression or involution of the Mullerian ducts (embryonic uterus and tubes) in the male fetus at the time of sexual differentiation. Although MIS was once thought to be only a fetal hormone, MIS production is now known to be present throughout life in males, and postnatally in females (where it is produced by granulosa cells once the Mullerian ducts have differentiated into the uterus and fallopian tubes). Accumulated evidence suggests that control of testicular descent is regulated by 2 different hormones, where MIS may initiate the transabdominal phase and androgens may stimulate the inguino-scrotal phase.

As used herein, MIS refers to MIS from any animal species, such as human, horse, sheep, pig, rat, mouse, etc. Principally, but without limitation, MIS refers to human MIS. The term MIS extends to naturally occuring allelic variants of the MIS protein sequence.

Human MIS has the sequence shown in (FIG. 3). Human and bovine MIS share considerable homology, particularly at the N-terminus. Bovine MIS is available by purification from neonatal calf testes and human recombinant MIS is available (non-commercially) from the laboratoty of Prof. P. K. Donahoe, Massachusetts General Hospital, Boston, U.S.A. The purification procedures for MIS are well known. Preferably MIS is produced by recombinant DNA methods.

Analogues of MIS or its proteolytic cleavage fragments which comprise amino acid sequence variants fall into one or more of three classes: substitutional, insertional and deletional variants. Insertions include amino acid and/or carboxyl terminal fusions as well as intra sequence insertions of single or multiple amino acids. Generally, insertions within the mature coding sequence of MIS or its proteolytic products will be smaller than those with the amino or carboxyl terminal fusions, of the order of say 1 to 4 residues.

Insertional amino acid sequence variants of MIS or its proteolytic products are those in which one or more amino acid residues are introduced into a predetermined site in the MIS protein or proteolytic "daughter" peptides.

Deletional variants are characterized by the removal of one or more amino acids from the MIS peptide sequence.

Amino acid substitutions are typically of single residues; insertions usually will be on the order of about 1–10 amino acid residues; and deletions will range from about 1–20 residues. Deletions or insertions preferably are made in adjacent pairs, ie: a deletion of 2 residues or insertion of 2 residues.

Substitutional variants are those in which at least one residue in the MIS sequence has been removed and a different residue inserted in it place. Such substitutions generally are made in accordance with the following Table 1.

TABLE 1

| Original Residue | Exemplary Substitutions |
|---|---|
| Ala | Ser |
| Arg | Lye |
| Axn | Gln; His |
| Aup | Glu |
| Cys | Ser |
| Gln | Asn |
| Glu | Asp |
| Gly | Pro |
| His | Asn; Oln |
| Ile | Leu; Val |
| Leu | Ile; Val |
| Lys | Arg; Oln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Lou |

Generally amino acids are replaced by other amino acids having like properties, such as hydrophobicity, hydrophilicity, electronegativity, bulky side chains, etc.

The amino acid variants of MIS or its proteolytic peptides referred to above may readily be made using peptide synthetic techniques well known in the art, such as solid phase peptide synthesis (Merrifield; J. Am. Chem. Soc., 85: p 2149, 1964) and the like, or by recombinant DNA manipulations upon the gene encoding MIS of any particular animal. Techniques for making substitution mutations at predetermined sites in DNA having known sequence are well known, for example M13 mutagenesis. The manipulation of DNA sequences to produce variant proteins which manifest as substitutional, insertional or deletional variants are well known in the art and are described for example in Maniatis et al (Molecular Cloning: A Laboratory Manual; Cold Spring Harbor Laboratory, 1982).

The above referenced amino acid sequence variants of MIS or its daughter peptides may all be regarded as analogues of MIS, if they possess MIS activity as is defined hereinafter. Human MIS contains several plasmin cleavage sites, around, for example, amino acid numbers 427 and 428. Cleavage around these sites may give rise to pharmacologically active peptides which may have MIS or other activity.

Any compound having MIS activity as defined hereinafter is regarded as an analogue of MIS. This includes small organic or inorganic drugs which may, for example, be designed to mimic the three dimensional structure or part thereof of MIS. Compounds of this type may be produced as a result of x-ray crystallography of MIS or its peptide fragments, or other three dimensional modelling techniques.

"MIS activity" is defined as the ability to effect germ cell transformation in animals having undescended testes. A convenient in vivo assay for MIS activity utilises an organ-culture system with neonatal rat/mouse testicular fragments, as adopted from Haneji et al (1991; J. Endocrinol. Mar 128 (3): 383–8). Testicular fragments are cultured in serum-free medium with various concentrations of rhMIS. Histological sections of the testis fragments are examined after 9 days, and the number of germ cells at various stages are counted per 100 Sertoli cells. In the presence of effective quantities of compounds having MIS activity, the germ cell transformation may be monitored by direct cell counts in this way.

MIS or its analogues should generally be administered under the guidance of a physician, and pharmaceutical compositions would usually contain an effective amount of MIS or an analogue thereof in conjunction with a conventional, pharmaceutically acceptable carrier, for example, as described in Remingtons Pharmaceutical Sciences, 17th Edition, Mack Publishing Company, Easton, Pa., Ed. Osol et al., which is incorporated herein by reference.

The pharmaceutical carrier employed may be, for example, either a liquid or a solid. Examples of liquid carriers include physiologically buffered saline, dextrose, sterile water, olive oil and the like. Similarly, the carrier may include time delay material well known to the art, such as glyceryl monostearate, ethyl cellulose, hydroxypropylmethyl cellulose, methylmethacrylate and the like. Examples of solid carriers are lactose, sucrose, talc, gelatin, agar, pectin, magnesium stearate, stearic acid and the like.

A wide variety of pharmaceutical forms can be employed. Injectable forms of MIS generally contain MIS dissolved in a sterile vehicle such as water, saline, dextrose or the like. Injectable solutions of MIS may contain, for example, to 10 ug to 500 mg per ml. Injectable solutions may be provided in ampule or vial or non-aqueous liquid suspension.

If a solid carrier is used, the preparation can be tableted, placed in a hard gelatin capsule or admixed with a slow release polymer to form a dosage form. The amount of solid carrier will vary widely but will preferably be from about 0.1 mg to 1 g.

Preferably, each parenteral dose of MIS containing pharmaceutical forms will contain a reactive ingredient in an amount form about 0.05 mg to about 500 mg. If oral dosage units are employed, they will contain the active ingredient in an amount of from about 0.05 mg to about 1.0 mg.

Medicaments or compositions may be prepared by admixing, dissolving, blending, grinding or the like, MIS with a pharmaceutically acceptable carrier or excipient according to methods well known in the art.

MIS is administered to such an animal in an effective amount. The term "effective amount" refers to an amount effective to cause germ cell maturation. It will be recognised by one of skill in the art that the form and character of the pharmaceutically acceptable carrier or diluent is dictated by the amount of active ingredient with which it is to be combined, the route of administration and other well known variables.

The route of administration of MIS or analogues thereof may be parenteral, topical, or oral. The term "parenteral" as used herein includes intravenous, intrascrotal, intratesticular, intramuscular or subcutaneous administration.

MIS may be administered transdermally, particularly to the scrotum, or skin which surrounds the descended or un-descended testes.

MIS or analogues thereof may be administered from an implantable or skin-adhesive sustained release article. Examples of suitable systems include copolymers of L-glutamic acid and -ethyl-L-glutamate (U. Sidman et al., 1983, "Biopolymers" 22, 1: 547–556), poly (2-hydroxyethyl-methacrylate) (R. Langer et al., 1981, J. Biomed. Matter. RES., 15: 167–277 and R. Langer et al. 1982, "Chem. Tech." 12: 98–105) or the like. Such articles may, for example, be implanted subcutaneously or placed in contact with the skin.

Animals which may be treated according to the present invention include humans, horses, and other domestic animals.

It will be recognised by one skilled in the art that the optimal quantity and spacing of individual dosages of MIS and analogues thereof will be determined by factors such as the route and site of administration, and the type and age of the particular animal being treated. By way of example only, MIS may be administered in an amount from 0.05 µg to about 500 mg per kg body weight. Dosage and frequency of administration of MIS or analogues thereof will often depend upon the judgement of a consulting physician or veterinarian in any particular case.

The optimal course of treatment, that is, the number of doses of MIS or analogues thereof given per day for a defined number of days, can be readily ascertained by those skilled in the art using conventional courses of treatment determination tests.

Generally, treatment with MIS or analogues thereof to effect germ cell maturation usually takes place shortly after surgical or hormonal treatment of undescended testes of an animal. In humans, it is preferred that treatment take place between four months and 2 years of age. However, animals of any age having undescended testicles may be treated according to the present invention. Alternatively MIS may be administered before testes descend to ensure proper germ cell maturation.

MIS may be administered in combination with one or more other agents such as CGRP (calcitonin gene related peptide) or testosterone. In co-pending Australian Patent Application No. PJ 9573/90, (which is incorporated herein by reference) we have described the action of CGRP in testicular descent. The co-administration of CGRP and MIS may cause testicular descent and germ cell maturation.

Testosterone may also have some as yet uncharacterised role in germ cell maturation, particularly as a pulse of testosterone production occurs shortly after birth.

Without limiting the invention, the applicant believes that MIS (or its peptide fragments) is the hormone which controls testicular germ cell maturation.

MIS may be intimately involved in sperm production and maturation. Thus, antagonists of MIS would be expected to block, or adversely effect sperm production.

The invention is further described, by way of example only, with reference to the following nonlimiting Figures and Examples:

Figure 1:
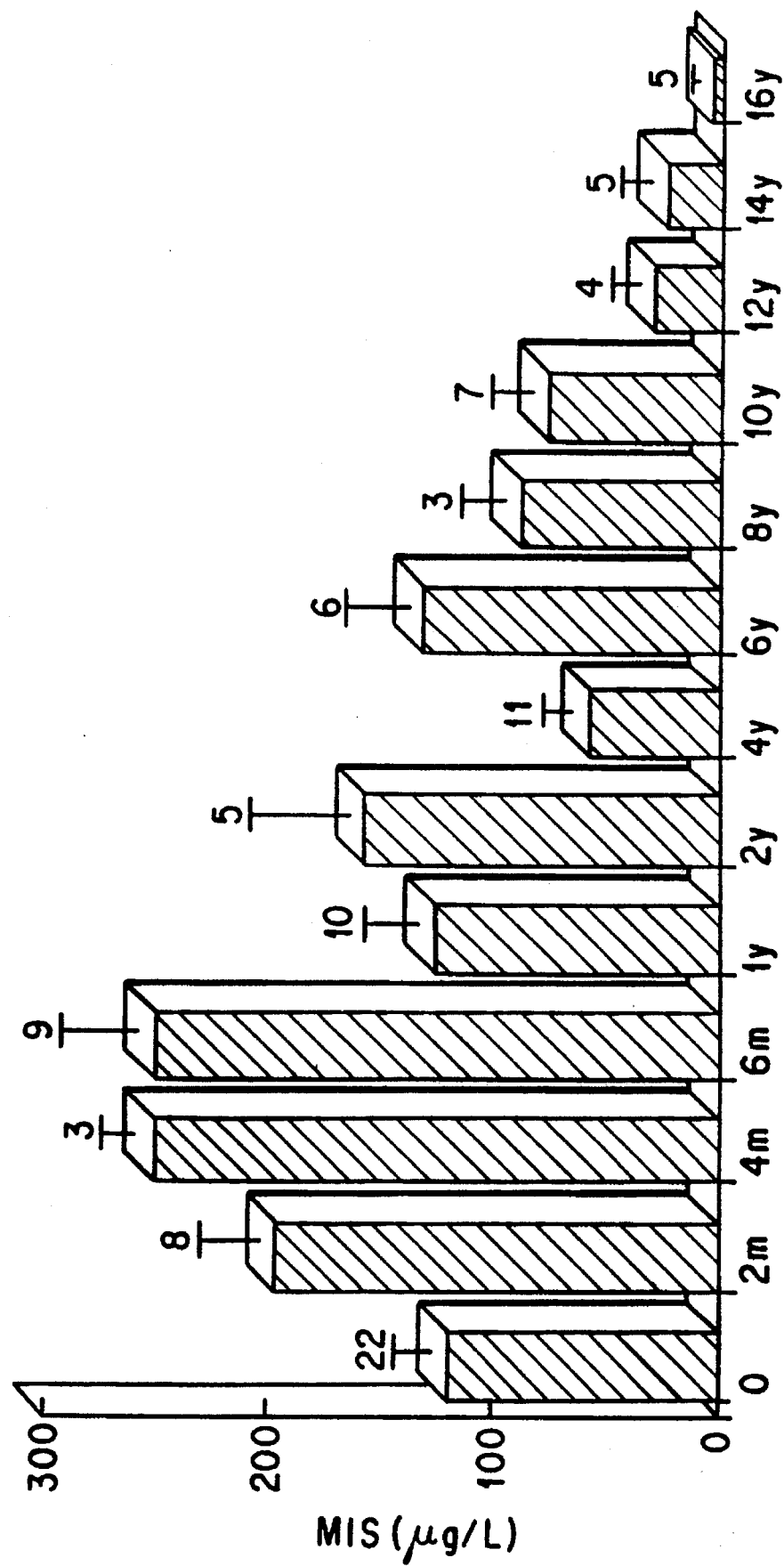
FIG. 1 shows mean serum MIS levels in boys as a function of age. The bars indicate the SEM, with the values above representing the number of subjects in each group.
Figure 2:
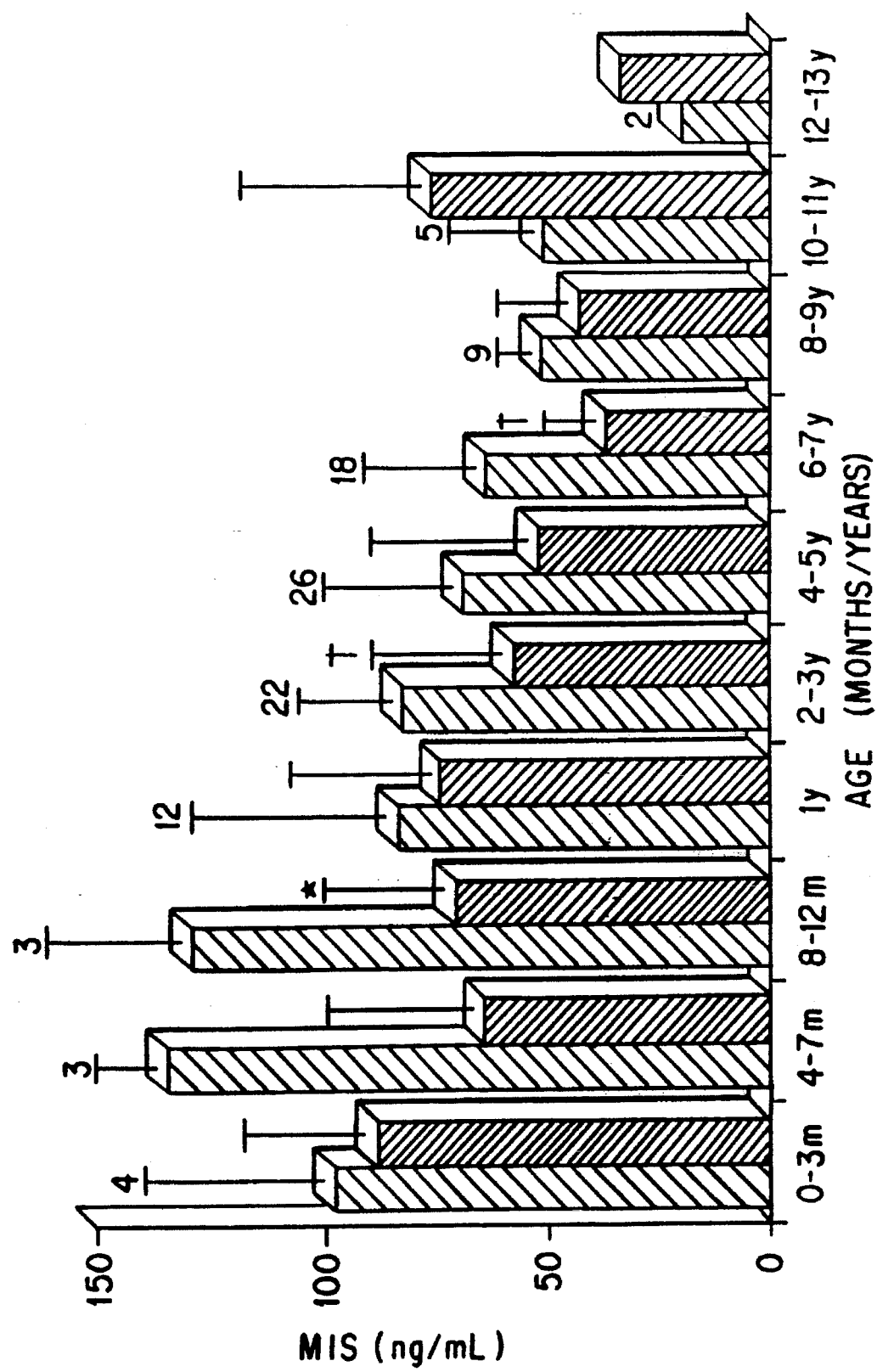
FIG. 2 is similar to FIG. 1 except that MIS levels in normal boys (<) and boys having undescended testes (■) are shown.

[The absolute MIS concentrations shown in FIGS. 1 and 2 are slightly different because of differing calibration of the assay. This does not affect the general outline of the histogram.]

FIG. 3 shows the nucleotide and predicted amino acid sequence of human Mullerian Inhibiting Substance. The nucleotide sequence of the mRNA strand is displayed from the 5' and 3' direction, with +1 being the 5' end of the mRNA. The promoter, 5' and 3' untranslated regions, and the introns are shown in lower case letters. The protein coding regions are shown in capitals. The putative TATA box at −27 is overlined, the polyadenylation signal at 2728 is bracketed, and the polyadenylation addition site of 2744 is marked by an asterisk. The heavy arrow indicates the cleavage that generates the mature protein, and the light arrow indicates the possible cleavage sites for the signal sequence.

EXAMPLE 1

Serum levels of MIS in boys from birth to 18 years were determined by immunoassay as set forth below.

Experimental subjects

Sera from patients at the Royal Children's Hospital, Melbourne, Australia, were collected from the Biochemistry Department. These samples had been collected for routine biochemical analyses and stored for 1 week at −20° C., after which time they are normally discarded. Sera were used for MIS determination at the end of the week's storage. The clinical diagnosis and/or reason for blood collection were examined to determine any possible correlations with MIS levels.

Experimental animals

BALB/c mice and New Zealand White rabbits were immunised to produce anti-MIS monoclonal and polyclonal antibodies.

MIS purification

Bovine MIS was purified from newborn calf testes. Minced testes were incubated in Ham's F-10 medium (Flow Laboratories, Melbourne, Australia) containing 20 mM HEPES and $10^{-5}$M phenylmethyl-sulfonylfluoride. After centrifigation the supernatant was precipitated with $(NH_4)_2SO_4$ (30–45%), and the resulting precipitate was purified further by wheat germ lectin chromatography (Sepharose, Pharmacia, Uppsala, Sweden), followed by hydrophobic interaction chromatography (phenyl-Superose, Pharmacia). The purified MIS fraction was tested for biological activity in a mouse bioassay according to Donahoe et al., 1988, J. Surg. Res. 23: 141–148, (incorporated herein by reference), except that fetal mice are used.

Immunoassay

Serum immunoassay of MIS was measured by sandwich enzyme immunoassay using an anti-MIS monoclonal antibody raised against purified bovine MIS (Hudson, P. et al., 1990, J. Clin. Endocrinol. & Metab., 80: 16–22; and Baker et al., 1990, J. Clin. Endocrinol. & Metab., 70: 11–14 which is incorporated herein in its entirety by reference) and a polyclonal antibody raised against recombinant human MIS (as described by Donahoe et al., 1977, J. Surg. Res. 23: 141–148).

Flat-bottomed 96-well Nunc Immunoplates (Nunc) were used as a solid support. Wells were coated with the anti-MIS monoclonal antibody(2.5 ug/mL in 50 mM carbonate buffer, pH 9.6) overnight at 4° C. After washing with PBST (0.01M phosphate buffer, 0.15M NaCl, 0.05% Tween-20, pH 7.4), standard and samples were incubated for 4 h at 37° C. Both standard and samples were diluted in a mixture of adult female sera and PBST, so that the final concentration of serum was 50% in all cases. rhMIS (recombinant human MIS) was used to construct a standard curve. After a second wash with PBST (three times), the IgG fraction of the rabbit antisera to rhMIS diluted in PBST (5 µg/mL) was added and incubated overnight at room temperature. A third wash with PBST (three times) was followed by incubation with horseradish peroxidase conjugated swine antirabbit Ig (Dakopatts, Glostrup, Denmark) for 1 h at room temperature. After a final wash with PBST, tetramethyl benzidine substrate was added, and the colour absorbance was recorded as described above. A standard curve was constructed for each assay using serial dilutions of rhMIS starting at 400 µg/L. Each sample was measured in duplicate at one or more dilutions depending on the amount of sample.

The specificity of the assay was tested using a number of hormones.

The above immunoassay is described by Baker et al. 1990, J. Clin. Endicronol. & Metab. 70: 11–14.

Statistics

The standard curve for the EIA was calculated by linear regression analysis, and slope and midrange concentrations were computed. Analysis of variance statistics were performed to compare the MIS value at birth with that at various ages.

MIS serum concentrations

The means of MIS serum concentrations from different age groups are shown in FIG. 1. The concentration of MIS in male serum appears to rise after birth until approximately 1 year of age and then decreases until after 16 years of age, when it is undetectable. There was no correlation with the clinical diagnoses, which included a large number of medical and surgical conditions, none of which was a genital anomaly.

The difference in MIS levels at 0–2 months and 4–12 months was found to be statistically significantly different, with $P<0.005$. The MIS levels after 14 years of age (when 14–16 years are compared with 0–2 months and when 16–18 years are compared with 0–2 months) were also statistically significantly different from the levels at 0–2 months ($P<0.025$).

These results clearly show high levels of MIS in the serum of boys aged from 4–12 months which is indicative of MIS function at this time. In addition, the MIS peak levels occur just after the post natal secretions of testosterone, which is documented at 0–4 months, with a peak at 1–3 months. Beyond 3–6 months of age, sexual development is in a quiescant phase, with few important events until the onset of puberty towards the end of the first 10 years of life. However, one significant event is the transformation of gonocytes to type A speratogonia in the post-natal testis, which occurs most rapidly at 3–5 months and about 1 week of age in the rat. This transformation is essential for normal spermatogenesis after puberty, and without it, infertility may occur. Since MIS concentrations normally are high during this period, this is a direct indication that MIS is involved with gonocyte development.

EXAMPLE 2

The relationship between MIS levels and cryptorchidism was investigated.

Blood samples were collected during anaesthesia from 104 children who underwent orchidopexy at Royal Children's Hospital, Melbourne, between Aug. 9, 1989 and Apr. 9, 1990. Samples from age-matched controls were taken from boys having minor non-testicular surgery, such as an inguinal herniotomy, umbilical hernia repair, circumcision, and so on. Pairs were matched by month for patients under 12 months old and by year beyond 1 year of age. Twenty-six age-matched sera were supplied from the Biochemistry Department of Royal Children's Hospital, Melbourne, because of the shortage of control sera. The clinical diagnoses were examined in all cases from the patients' clinical records. All cryptorchid boys were carefully examined under anaesthesia preoperatively where the cremasteric reflex was eliminated and the retractile testis were easily differentiated from cryptorchidism. A testis was considered undescended when it could not be brought into the lower scrotum. No retractile testis or ectopic testis was included in this study.

Serum MIS-immunoreactivity was measured by sandwich enzyme immunoassay as set forth in Example 1.

The total of 104 patients consisted of 28 boys with bilateral cryptorchidism and 76 children with unilateral undescended testis. None of the patients had any serious systemic disorder or urogenital anomaly apart from cryptorchidism. The mean serum MIS concentrations of different age groups derived from boys with cryptorchidism as well as paired, age-matched boys are shown in FIG. 2. The MIS levels of age-matched controls showed an increase after birth with a peak at 4–12 months of age and then decreased with age. MIS values of patients with undescended testes also declined with age, but without an apparent surge in the first year. MIS concentrations of cryptorchid boys were significantly lower than controls at 8–12 months ($71\pm34$ v $129\pm73$ ng/mL, $p<0.05$), 2–3 years ($57\pm32$ v $82\pm25$ ng/mL, $P<0.01$), and 6–7 years ($37\pm13$ v $64\pm32$ ng/mL, $P<0.01$) of age. At other ages no statistical significance could be shown. The mean MIS value derived from all cryptorchid samples ($55\pm33$ ng/mL) was significantly lower ($P<0.001$) compared with that from controls ($74\pm37$ ng/mL). The mean MIS levels of patients with bilateral cryptorchidism ($45<30$ ng/mL) was significantly lower ($P<0.05$) than that of patents with unilaterial undescended testis ($59\pm33$ ng/mL), although there was not a significant difference in average age between those two groups ($4.8\pm2.8$ years v $4.3\pm3.1$ years). The overall interassay variability for 10 assays was 14.3%.

The above results document lower MIS levels in patients with cryptorchidism compared with paired age-matched controls.

This depression of MIS between 4–12 months in human males with undescended testis, and in whom germ cell maturation is abnormal directly implicates a role for MIS in the prevention of abnormal germ cell maturation in males with undescended testis. MIS supplements could be administered to human males with undescended testis to prevent abnormal germ cell maturation. In addition to or alternatively, following surgery or other procedures to locate testes in the scrotum, MIS therapy may be carried out to facilitate normal germ cell maturation.

The role of MIS in germ cell maturation as indicated herein is supported by a number of observations.

Sertoli cells (the cells that produce MIS) are responsible for differentiation of male germ cells since they undergo spermatogenesis only when inside the testis cords (see Zamboni et al., 1983, J. Exp. Biol. 228: 173–93; Jost, 1972, Arc. Anat. Microsc. Morphol. Exp. 61: 415–38. High levels of MIS mRNA are present on day 1 in rat testis, with moderate levels between days 3–7. These MIS levels suggest active MIS secretion at the same time as germ cell maturation in the rat occurs (Kuroda et al., 1900, Endocrinology 127: 1825–32).

MIS immunohistochemistry of $B^6$ $y^{dom}$ ovotestes from intersex mice show a very close correlation between the arrest of fetal germ cells at the prespermatogonia stage and MIS production of adjacent somatic cells. This observation is consistent with the hypothesis that MIS is involved in regulating male germ cell differentiation (data not shown).

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

We claim:

1. A method for the treatment of infertility associated with undescended testes in a male mammal which results from non-maturation of testicular germ cells, comprising (a) administering postnatally to a male mammal in need of said treatment a testicular germ cell maturing effective amount of at least one Muellerian inhibiting substance (MIS), optionally in association with a pharmaceutically acceptable carrier or excipient, and (b) performing surgical or hormonal treatment of said animal to effect testis descent.

2. The method according to claim 1, wherein said administering is performed after surgical or hormonal treatment of said mammal to effect testis descent.

3. The method according to claim 1, wherein said administering is performed on said mammal before testis descent.

4. The method according to claim 1, wherein said administering is performed in a manner selected from the group consisting of parenterally, topically and orally.

5. The method according to claim 4, wherein said administering is parenteral administration selected from the group consisting of intravenous, intramuscular, subcutaneous, intrascrotal and intratesticular administration.

6. The method according to claim 4, wherein said administering is topically by transdermal administration to scrotum or skin which surrounds descended or undescended testis of said mammal.

7. The method according to claim 4, wherein said administering is performed (a) parenterally from an implantable sustained release article; or (b) topically from a skin-adhesive sustained release article.

8. The method according to claim 1, wherein said male mammal is selected from the group consisting of a human, horse and a domestic animal.

9. The method according to claim 1, wherein said administration further comprises co-administration with a therapeutically effective amount of a calcitonin gene related peptide (CGRP).

10. The method according to claim 9, wherein said co-administration of said CGRP and said MIS is sufficient to effect at least one of testicular descent and germ cell maturation.

11. The method according to claim 1, wherein said administration further comprises co-administration with a therapeutically effective amount of testosterone.

12. The method according to claim 11, wherein said co-administration of testosterone and said MIS is sufficient to effect at least one of testicular descent and germ cell maturation.

13. The method according to claim 8, wherein said domestic mammal is selected from the group consisting of a sheep, pig, rat and mouse.

14. A method for effecting testicular germ cell maturation in a male mammal, comprising (a) administering postnatally to a male mammal having non-maturation of testicular germ cells a testicular germ cell maturing effective amount of at leat one Muellerian inhibiting substance (MIS), optionally in association with a pharmaceutically acceptable carrier or excipient, and (b) performing surgical or hormonal treatment of said mammal to effect testis descent.

15. The method to claim 14, wherein said administering is performed after surgical or hormonal treatment of said mammal to effect testis descent.

16. The method according to claim 14, wherein said administering is performed before testis descent in said mammal.

17. The method according to claim 14, wherein said administering is performed in a manner selected from the group consisting of parenterally, topically and orally.

18. The method according to claim 17, wherein said administering is parenteral administration selected from the group consisting of intravenous, intramuscular, subcutaneous, intrascrotal and intratesticular administration.

19. The method according to claim 17, wherein said administering is performed topically by transdermal administration to scrotum or skin which surrounds descended or undescended testis of said mammal.

20. The method according to claim 17, wherein said administering is performed (a) parenterally from an implantable sustained release article; or (b) topically from a skin-adhesive sustained release article.

21. The method according to claim 14, wherein said male mammal is selected from the group consisting of a human, horse and a domestic mammal.

22. The method according to claim 14, wherein said administering further comprises co-administration of a therapeutically effective amount of a calcitonin gene-related peptide (CGRP).

23. The method according to claim 22, wherein said co-administration of said CGRP and said MIS or analogue is sufficient to effect at least one of testicular descent and germ cell maturation.

24. The method according to claim 14, wherein said administering further comprises co-administration of therapeutically effective amount of a testosterone.

25. The method according to claim 24, wherein said co-administration of testosterone and said MIS is sufficient to effect at least one of testicular descent and germ cell maturation.

26. The method according to claim 21, wherein said domestic mammal is selected from the group consisting of a sheep, pig, rat and mouse.

27. The method according to claim 14, wherein said at least one carrier or excipient is in a pharmaceutically acceptable form.

28. A method for effecting maturation of mammalian testicular germ cells, comprising contacting said germ cells with a germ cell maturation effective amount of a germ cell composition comprising MIS, optionally in association with an acceptable carrier or excipient.

29. The method according to claim 28, wherein said carrier or excipient is in pharmaceutically acceptable form.

* * * * *